United States Patent

Hyon et al.

[11] Patent Number: 6,103,778
[45] Date of Patent: Aug. 15, 2000

[54] ADHESIVE COMPOSITION FOR SURGICAL USE

[75] Inventors: Suong-Hyu Hyon; Naoki Nakajima, both of Kyoto, Japan

[73] Assignee: BMG Inc., Kyoto, Japan

[21] Appl. No.: 09/162,491

[22] Filed: Sep. 28, 1998

[30] Foreign Application Priority Data

Feb. 12, 1998 [JP] Japan ................... 10-069203

[51] Int. Cl.$^7$ .................. C08L 67/00; A61K 31/765
[52] U.S. Cl. ................... 523/111; 523/118; 524/539; 525/411; 525/412; 525/415; 525/450
[58] Field of Search ................... 523/111, 118; 524/539; 525/411, 412, 415, 450

[56] References Cited

U.S. PATENT DOCUMENTS

| | | | |
|---|---|---|---|
| 4,804,691 | 2/1989 | English et al. | 523/118 |
| 5,514,371 | 5/1996 | Leung et al. | 526/300 |
| 5,550,172 | 8/1996 | Regula et al. | 523/118 |

FOREIGN PATENT DOCUMENTS 3273679  11/1988  Japan ................... 523/118

OTHER PUBLICATIONS

Odian, George, *Principles of Polymerization*, 2d Ed., New York, Wiley & Sons, 1981, p. 21.

*Primary Examiner*—Andrew E. C. Merriam
*Attorney, Agent, or Firm*—Jordan and Hamburg LLP

[57] ABSTRACT

An adhesive composition for surgical use including an α-cyanoacrylate adhesive composition with a polymer characteristic for biodegrading and bioabsorbing the adhesive into the body of a living organism. It is preferred that the polymer is a co-polymer of DL-lactic acid and ε-caprolactone or a co-polymer of DL-lactic acid, ethylene glycol and ε-caprolactone, or a co-polymer of ethylene glycol and ε-caprolactone.

4 Claims, 2 Drawing Sheets

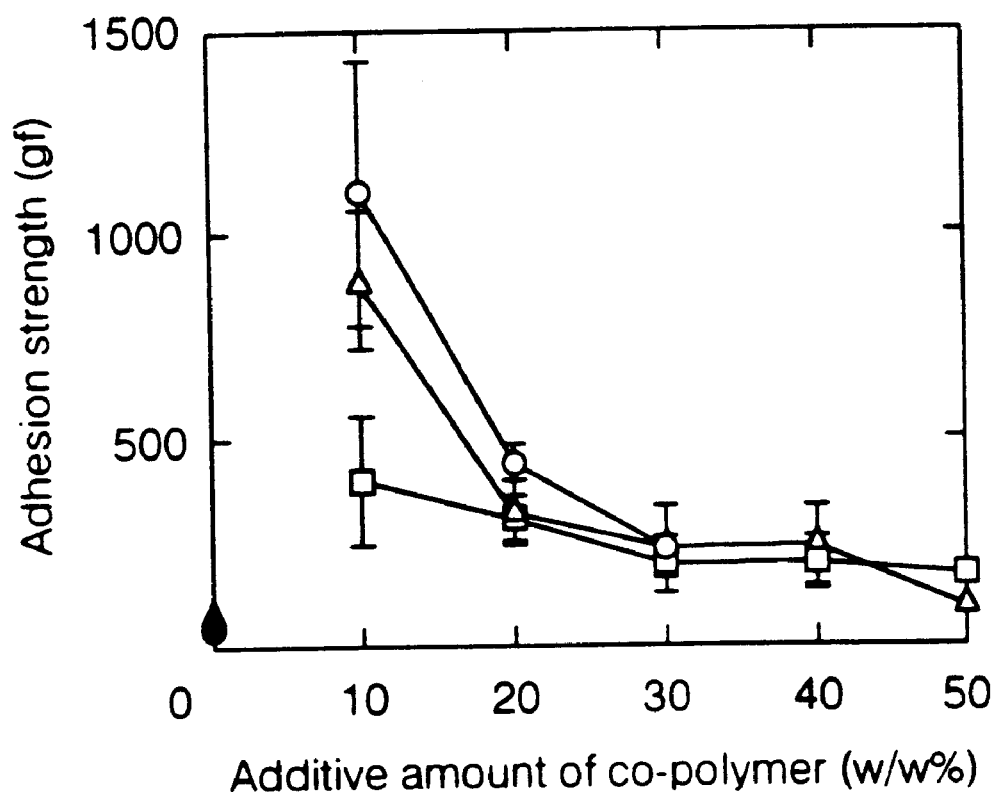
Fig. 1 Adhesion Properties of Novel Adhesive
Molecular Weight of co-polymer ; $1 \times 10^5$(○),
$6 \times 10^4$(△), $4 \times 10^4$(□), Biobond (●), Fibrin (▲)

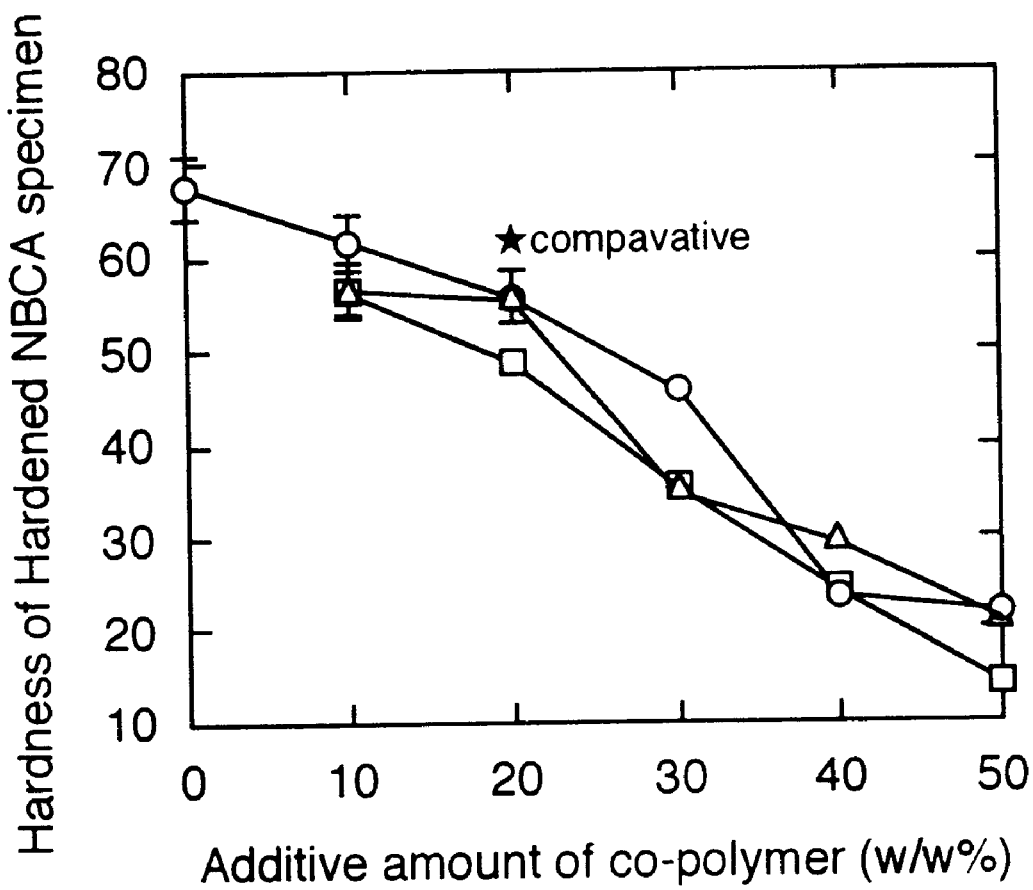
Fig. 2 Hardness of Hardened Novel Adhesive after Polymerization ; $1\times10^5$(o), $6\times10^4$(△), $4\times10^4$(□)

ADHESIVE COMPOSITION FOR SURGICAL USE

BACKGROUND OF THE INVENTION

1. Field of The Invention

The present invention relates to adhesive compositions for surgical use. More particularly, it relates to novel compositions, which are adjusted to have a suitable viscosity and a reduced cytotoxicity. The novel compositions have a softness similar to the soft tissue of a living organism and are easily biodegraded and bioabsorbed into the living organism at a moderate speed after healing. These novel compositions result from improving α-cyanoacrylate adhesive composition.

2. Description of The Related Art

Suturing and anastomosis of a wound is one of the most important operating techniques in any surgical operation. Therefore, the healing speed of the wound makes most of the difference between a good or a poor operation. Nowadays, the material compositions and operating methods for improving the speed of healing are continuously improving. For example, there have been improvements in methods for suturing a wound, and many good sutures have become readily available as a result. However, special techniques are still necessary in operations involving microvascular anastomosis and nerve sutures. Therefore, new inventions concerning adhesive methods for use in the living body system are needed to shorten surgical operations. There are many proposed reports and inventions all over the world for the above purpose.

The α-cyanoacrylate adhesive compositions are already widely sold in the market as adhesive compositions for surgical use. However, they remain of limited use in special clinical applications, because they often leak due to the low viscosity of the composition. The leakage sometimes damages the soft tissue. Additionally, these adhesive composition have a high cytotoxicity for the living cell.

The inventors of this patent have already disclosed several means (JP. Pat. 116409/1995) to remedy the above defects. This patent concerns new compositions for surgical use, in which a homo-polymer of lactic acid (DL-, D- and L- type), a co-polymer of lactic acid and glycolic acid or a co-polymer of lactic acid and ε-caprolactone are added to the α-cyanoacrylate adhesive composition as a thickening agent and a stabilizer. The resulting composition is easily biodegradable and bioabsorbable into the body of the living organism.

However, this patent fails to disclose the cytotoxicity of the surgical adhesive composition for the living cell, and, therefore, the cytotoxicity for the living cell is still uncertain. Weight-average molecular weights of the homo-polymer of DL-lactic acid and the co-polymer of lactic acid and ε-caprolactone are about 140,000 and 220,000 respectively, which is a relatively high molecular weight, so they are suitable as a thickening agent. The patent also fails to disclose the effects of molecular weight on plasticizing after hardening, and the hydrolyzing velocity of co-polymer compositions of lactic acid and ε-caprolactone when employed as a thickening agent.

SUMMARY OF THE INVENTION

The present invention proposes a novel adhesive composition for surgical use adding a polymer characteristic to an α-cyanoacrylate adhesive composition to biodegrade and bioabsorb it into the body of a living organism. It is preferred that the polymer is a co-polymer of DL-lactic acid and an ε-caprolactone, or a co-polymer of DL-lactic acid, ethylene glycol and ε-caprolactone, or a co-polymer of ethylene glycol and ε-caprolactone. It is highly preferred that the ratio of the composition is in the range of 70:30 to 30:70, that the weight-average molecular weight of the co-polymer of DL-lactic acid and ε-caprolactone are 10,000 to 120,000, and that the concentration of the co-polymer is in the range of 1 to 50 weight by weight percent. It is also preferred that the glass transition temperature of the polymer is in the range from 0 to −30° C.

The novel adhesive compositions of the invention can be easily adjusted to any degree of thickening agent to control viscosity. The hardened polymer, after polymerization, exhibits a softness and has an affinity to the body of a living organism, such as blood vessels, skin and viscera. It is possible that wider applications can be added to former uses of α-cyanoacrylate, because the composition is widely applied to hemostasis.

BRIEF DESCRIPTION OF THE DRAWINGS

FIG. 1 is a schematic view illustrating the adhesion properties between swine skin and n-butyl-cyanoacrylate (NBCA) by adding polymers of various weight-average molecular weights of DL-lactic acid and ε-caprolactone (mole ratio of 50:50 by DL-lactic acid and ε-caprolactone), and also illustrating comparison of adhesion strengths with adhesive sold in the market, such as, "Biobond" (fabricated by Yoshitomi Ph.) and "Fibrin Glue" (fabricated by Fujisawa Ph.).

FIG. 2 is a schematic view illustrating the hardness of a hardened NBCA specimen after polymerization according to the addition of various weight-average molecular weights of DL-lactic acid and ε-caprolactone (mole ratio of 50:50 by DL-lactic acid and ε-caprolactone). The vertical axis shows the Shore Hardness of a D type.

DETAILED DESCRIPTION OF THE INVENTION

The present invention relates to novel adhesive compositions of α-cyanoacrylate for surgical use, which have a suitable viscosity, reduced cytotoxicity to cells, a softness similar to the soft tissue of a living organism, and which are easily biodegraded and bioabsorbed into the body of the living organism at a moderate speed after healing.

Essentially, healing a wound in a living organism involves hyperplasia of the connective tissue by a renaturation ability in the living organism. Therefore, it is preferable to apply an adhesive, rather than to suture, to fix and support the connective tissue, in order not to prevent the restoration ability of the living organism during the week or 10 days necessary to finally heal the wound. In other words, the role of the preferred adhesive is to fix and adhere the wound during the period needed to complete the healing process, and then easily biodegrade, and bioabsorb into the body of the living organism and disappear soon thereafter. In addition, it is also important and necessary that biodegraded products of the adhesive are not poisonous or dangerous. The preferable qualities for an adhesive in a living organism include the following:

1) The ability to adhere at room temperature (bodily temperature) under conditions of high humidity and when in contact with fat.
2) The ability to combine enough tensile strength with softness in the hardened product, especially when adhering a wound on the face.

3) Exhibiting no tissue toxicity and no carcinogenesis, and causing little reactionary resistance as a foreign body.
4) Not interfering with the healing of a wound in a living organism.
5) The ability to biodegrade and be expelled through the living organism after healing.
6) The ability to be sterilized.
7) The ability to be easily manipulated and quickly applied to the wound.

It is believed that an adhesive satisfying the above conditions is the best adhesive for use in surgical applications. The present invention proposes novel compositions of an improved α-cyanoacrylate adhesive composition for surgical use, which has a suitable viscosity, reduced cytotoxicity, a softness similar to the soft tissue of a living organism, and which is easily biodegraded and bioabsorbed into the body of the living organism at a moderate speed after healing.

In order to meet the above criteria, the present invention is a novel adhesive composition for surgical use, which is prepared by adding polymers to an αcyanoacrylate adhesive composition to provide an easily biodegrading and bioabsorbing adhesive composition. The polymers include the co-polymer of DL-lactic acid and ε-caprolactone or the co-polymer of DL-lactic acid, an ethylene glycol and ε-caprolactone, or the co-polymer of the ethylene glycol and ε-caprolactone.

A most important factor for the surgical use of the adhesive concerns the cytotoxicity of the living cell. In other words, the adhesive composition must be safe for a living cell. Therefore, the adhesive composition has to be reduced to the level of cytotoxicity, of the living cell, when applied as a surgical adhesive.

Moreover, it is difficult to increase the additive amount and adjust the thickening agent to a suitable degree by adding polymers, when the polymers have a weight-average molecular weight of more than 140,000, because the additive amount depends on the molecular weight. Therefore, it is preferred that a co-polymer of DL-lactic acid and ε-caprolactone have a weight-average molecular weight within a range from 10,000 to 120,000.

A co-polymer having a weight-average molecular weight of less than 10,000 shows poor properties as a polymer, such as an adhesive, while it is possible to increase the additive amount. Furthermore, it is difficult to get a soft hardened polymer with a high speed of biodecomposition and bioabsorption into a living organism when employing a high weight-average molecular weight polymer. As previously mentioned, the speed of biodecomposition and bioabsorption largely depends upon the molecular weight and crystallinity of the polymer. It is preferable to employ a polymer having low molecular weight and crystallinity in order to improve the properties of biodecomposition and bioabsorption. In the case of a co-polymer of DL-lactic acid and ε-caprolactone, the glass transition temperature largely depends on the composed ratio of the co-polymer. Therefore, when a DL-lactic acid ratio in the co-polymer is more than 70%, the glass transition temperature of the co-polymer is greater than 0° C. On the other hand, when the ε-caprolactone ratio in the co-polymer is more than 70%, the glass transition temperature of the co-polymer is lower than 0° C., but the co-polymer changes hardness according to the degree of crystallinity. In conclusion, the preferable mole ratio of the DL-lactic acid to ε-caprolactone in the co-polymer composition is in the range of from 70:30 to 30:70 based on the crystallinity and the softness of the co-polymer.

Furthermore, the co-polymer of DL-lactic acid, ethylene glycol and ε-caprolactone, and the co-polymer of ethylene glycol and ε-caprolactone can be employed to improve the α-cyanoacrylate surgical adhesive. It is preferred that the molecular weight is within a range of from 10,000 to 200,000 and the composed ratio is within a range for preventing the crystallization of the co-polymer.

In this invention, the co-polymers employed to improve the viscosity and the softness after hardening α-cyanoacrylate are synthesized from lactic acid as a raw material, which widely disperses not only in the living body but also in nature, and ε-caprolactone, which is widely used as a raw material for polyurethane, available for both household and industrial use. These raw materials are ordinarily eliminated in the metabolism of the living body and exhibit no poisonous qualities. Furthermore, co-polymers of DL-lactic acid and ε-caprolactone are already employed as sutures in medical use applications. Polyethylene glycol exhibits no poisonous qualities and can possibly be eliminated from the body when the polymer has a molecular weight of less than several ten thousands, in spite of having poor biodecomposability.

The co-polymer of DL-lactic acid and ε-caprolactone employed in the invention is soft, even at room temperature, and looks like rubber because the weight-average molecular weight is in a relatively low range of 10,000 to 120,000. Not only is the hardened co-polymer soft, but also the adhesive viscosity can be changed to any level by adding α-cyanoacrylate. It is possible to reduce the usage of poisonous α-cyanoacrylate when adjusting to an intensive softness and viscosity. The amount of α-cyanoacrylate can be reduced by employing, as a thickening agent, a relatively low molecular co-polymer having a weight-average molecular weight of less than 120,000. The cytotoxicity to the living cell is thus reduced to the same level as with the co-polymer of polyethylene glycol.

EXAMPLES

Example 1

FIG. 1 is a schematic view illustrating the changes in adhesion properties between swine skin (about 1×3 cm) and an NBCA specimen as a result of adding polymers of various weight-average molecular weights of DL-lactic acid and ε-caprolactone (a molecular ratio of 50:50 of DL-lactic acid and ε-caprolactone at a glass transition temperature of about −8° C.). The adhesion property was measured as follows.

1) First, about 10 μl of the adhesive was applied to the swine skin surface (about 1×1 cm).
2) The treated swine skin surface was adhered to an untreated swine skin surface.
3) A load of about 500 g was applied to the swine skin surfaces for 1 minute.
4) The peeling strength of the two surfaces was measured at a rate of 10 mm/min. by a tensile tester (fabricated by Shimazu Co.) to estimate adhesion strength.

FIG. 1 also illustrates comparison of adhesion strengths with adhesives sold on the market, such as, "Biobond" (fabricated by Yoshitomi Ph.) and "Fibrin Glue" (fabricated by Fujisawa Ph.). The adhesion strengths gradually decrease in accordance with an increase in the amount of co-polymer and a decrease in molecular weight, but, even so, the results are excellent compared to known adhesives.

Example 2

Table 1 below shows the initial viscosity (CP, centipoise) of an NBCA specimen after addition of a co-polymer of about 100,000 weight-average molecular weight of DL-lactic acid and ε-caprolactone (a mole ratio of 50:50 DL-lactic acid and ε-caprloactone). The viscosity was measured at 25° C. and 1 atm by a B-type rotating viscometer (fabricated by Tokyo Keiki). The viscosity of the adhesives is excellent in comparison with those of "Biobond" or "Aron-alpha" (fabricated by Sankyo Ph.).

TABLE 1

Viscosity of Novel adhesive

|  |  | Viscosity (CP) |
|---|---|---|
| Aron-Alpha |  | 59 |
| Biobond |  | 3,560 |
| NBCA + co-polymer |  |  |
| co-polymer | 10% | 843 |
|  | 15% | 7,560 |
|  | 20% | 30,000 |

Example 3

FIG. 2 is a schematic view illustrating the hardness of a hardened NBCA specimen after polymerization based on the addition of various weight-average molecular weights of DL-lactic acid and ε-caprolactone (a mole ratio of 50:50 DL-lactic acid and ε-caprolactone). The hardness was measured as follows:

1) The specimens were fabricated by polymerization and hardening of the co-polymer for 3 days at 60° C. in a vessel containing water.

2) They were pressed at 140° C. by hot pressing.

3) They were formed into a disc 30 mm in diameter and 5 mm thick.

4) The hardness of the specimen was measured by a Shore Hardness Tester of a D-type (fabricated by Kohbunshi Keiki).

The hardness is 68 when co-polymer is not added, but gradually decreases as the amount of co-polymer increases, and as the molecular weight of the same amount of the co-polymer decreases. The adhesives remain suitably flexible even after hardening.

Example 4

Table 2 below shows test data concerning the cytotoxicity, for a living cell, of an NBCA specimen after adding co-polymers of DL-lactic acid of about 60,000 weight-average molecular weight and ε-caprolactone (with a mole ratio of 50:50 DL-lactic acid and ε-caprolactone and a glass transition temperature of about −9° C.). Neutral Red 50 (NR50) was defined as a reagent concentration value when the cytoactivity is decreasing until one half of the original cytoactivity value. Thus, high toxicity means a low NR50 value. The test method is described as follows:

1) The hardened co-polymers and their blends of 0.5 g were added to a phosphoric acid buffer solution of 3 ml.

2) They were heated for 1 hour at 120° C.

3) A solution extracted from the specimen was subjected to a poison test.

4) The test procedure followed the reference, J. Biomed. Mater. Res., 29, 829–834 (1995), and the cytotoxicity was evaluated based on the amount of Neutral Red diffused into the cell.

TABLE 2

Cytotoxicity of Novel Adhesive

|  |  | NR50 (ppm) |
|---|---|---|
| Histoacryl |  |  |
| Composite |  | 611 ± 6 |
| Hardened Composite |  | 994 ± 6 |
| NBCA + co-polymer |  |  |
| co-polymer | 10% |  |
| Composite |  | 744 ± 6 |
| Hardened Composite |  | 1,098 ± 29 |
| co-polymer | 30% |  |
| Composite |  | 967 ± 9 |
| Hardened Composite |  | 1,553 ± 12 |

All cytotoxicity data on the specimens, namely their component elements, their co-polymers and their blends are shown in Table 2 and compared with an n-butyl-cyanoacrylate of "Histoacryl" (fabricated by B. Braun and sold in the market). It is clear that the values of all the specimen are far lower than "Histoacryl".

The hardened adhesives prepared by the method described in Example 1 were implanted on the back subcutaneous tissue of 20-week-old rabbits. When the implanted portion was observed after 3 months, the adhesives were perfectly biodegraded and bioabsorbed and there was no tissue reaction in the ambient parts owing to the adhesive composition.

Comparative Example

Co-polymers of DL-lactic acid and ε-caprolactone (a mole ratio of 80:20 DL-lactic acid and ε-caprolactone, of about 220,000 weight-average molecular weight and a glass transition temperature of about −8° C.) were added to an NBCA as a thickening agent to fabricate the hardened adhesives as described in Example 3. The Shore Hardness was measured and it showed a high value of about 63 as described in FIG. 2. The NR50 of the adhesive had a high cytotoxicity, value of 998+−13 (ppm) following the test method described in Example 4.

The adhesives were implanted on the back subcutaneous tissue of 20-week-old rabbits. When the implanted portion of the tissue was observed after 3 months, about 20%, by weight percent, of the adhesives still remained in the implanted portion, which means biodegradation and bioabsorption were too slow. Inflammation was observed in ambient tissue owing to the presence of the adhesive composition.

Example 5

A co-polymer of ε-caprolactone of about 140,000 weight-average molecular weight and polyethylene glycol (mole ratio of 50:50 of ε-caprolactone and polyethylene glycol and a glass transition temperature of about −22° C.) was prepared. An adhesive was fabricated from NBCA and a co-polymer of about 20%, by weight percent, as an additive. The peeling strength of the adhesion properties was tested in the same manner as Example 1. The peeling strength, the hardness, and NR50 of the hardened adhesive were about 420 gf, about 56, and about 1,000, respectively.

What we claim is:

1. An adhesive composition comprising an α-cyanoacrylate adhesive composition and a co-polymer of ethylene glycol and ε-caprolactone, the weight-average molecular weight of the co-polymer ranging from 10,000 to 200,000, and the adhesive composition of said α-cyanoacrylate adhesive composition and said co-polymer being biodegradable and bioabsorbable into a body of a living organism.

2. An adhesive composition comprising an α-cyanoacrylate adhesive composition and a co-polymer of DL-lactic acid, ethylene glycol and ε-caprolactone, the adhesive composition of said α-cyanoacrylate adhesive composition and said co-polymer being biodegradable and bioabsorbable into a body of a living organism.

3. An adhesive composition comprising an α-cyanoacrylate adhesive composition and a co-polymer of ethylene glycol and ε-caprolactone, the adhesive composition of said α-cyanoacrylate adhesive composition and said co-polymer being biodegradable and bioabsorbable into a body of a living organism.

4. The composition of claim 2 wherein the weight average molecular weight of said co-polymer is within the range of from 10,000 to 200,000.

* * * * *